US008884069B2

(12) United States Patent
Camera Roda et al.

(10) Patent No.: US 8,884,069 B2
(45) Date of Patent: Nov. 11, 2014

(54) PRODUCTION OF ALDEHYDES BY OXIDATION IN AQUEOUS MEDIUM WITH SELECTIVE RECOVERY OF THE PRODUCT BY MEANS OF PERVAPORATION

(75) Inventors: Giovanni Camera Roda, Bologna (IT); Vincenzo Augugliaro, Bologna (IT); Vittorio Loddo, Bologna (IT); Giovanni Palmisano, Bologna (IT); Leonardo Palmisano, Bologna (IT)

(73) Assignee: Alma Mater Studiorum Universita di Bologna, Bologna (IT)

( * ) Notice: Subject to any disclaimer, the term of this patent is extended or adjusted under 35 U.S.C. 154(b) by 0 days.

(21) Appl. No.: 13/703,618

(22) PCT Filed: Jun. 10, 2011

(86) PCT No.: PCT/IB2011/052541
§ 371 (c)(1),
(2), (4) Date: Jan. 29, 2013

(87) PCT Pub. No.: WO2011/154925
PCT Pub. Date: Dec. 15, 2011

(65) Prior Publication Data
US 2013/0123546 A1    May 16, 2013

(30) Foreign Application Priority Data

Jun. 11, 2010  (IT) .............................. RM2010A0319

(51) Int. Cl.
*C07C 45/27* (2006.01)
*C07C 45/29* (2006.01)
*B01J 19/08* (2006.01)
*B01J 8/00* (2006.01)
*C07C 45/36* (2006.01)
*C07C 45/78* (2006.01)
*C07C 45/38* (2006.01)

(52) U.S. Cl.
CPC ................. *C07C 45/27* (2013.01); *C07C 45/29* (2013.01); *C07C 45/36* (2013.01); *C07C 45/78* (2013.01); *C07C 45/38* (2013.01)
USPC ........... 568/438; 422/186; 422/187; 422/608; 204/157.93

(58) Field of Classification Search
CPC ...................................... B01J 19/123
USPC .......................... 568/438; 422/186, 187, 608; 204/157.93
See application file for complete search history.

(56) References Cited

FOREIGN PATENT DOCUMENTS

DE      4337231 A1     5/1995
WO   2009130245 A1    10/2009

OTHER PUBLICATIONS

International Search Report and Written Opinion in PCT application PCT/IB2011/052541, mailed Nov. 11, 2011.
Solovieva A B et al., "Catalytic process of alcohol oxidation with target product pervaporation", J. of Membrane Science, Feb. 21, 1996.
Palmisano et al., "Photocatalytic selective oxidation of 4-metxybenzyl alcohol to aldehyde in aqueous suspension of home-prepared titanium dioxide datalyst", Advanced Synthesis and Catalysis, vol. 349, No. 6, Apr. 17, 2007, pp. 964-970.

*Primary Examiner* — Sikarl Witherspoon
(74) *Attorney, Agent, or Firm* — Kristina Castellano; Castellano PLLC

(57) ABSTRACT

A process for the preparation of an aromatic aldehyde by means of the oxidation of the corresponding starting compound in aqueous medium, and separation of said aldehyde from said medium by pervaporation is disclosed together a plant for its carrying out. Advantageously, the process of the present invention allows control of oxidation reaction and recovery of the product with high selectivity and purity. Among others, benzaldehyde, anisaldehyde and vanillin can advantageously be prepared by this process.

20 Claims, 15 Drawing Sheets

PRODUCTION OF ALDEHYDES BY OXIDATION IN AQUEOUS MEDIUM WITH SELECTIVE RECOVERY OF THE PRODUCT BY MEANS OF PERVAPORATION

CLAIM FOR PRIORITY

This application is a U.S. National Stage Application of PCT/IB2011/052541 filed on Jun. 10, 2011, which claims priority to Italian Patent application RM2010A000319 filed Jun. 11, 2010, the contents of both of which are incorporated herein by reference.

The present invention relates to the field of organic chemistry and in particular to a process for the preparation of an aromatic aldehyde comprising the oxidation of a corresponding compound and separation of said aldehyde by means of pervaporation.

BACKGROUND OF THE INVENTION

The synthesis of organic compounds, as in general many chemical processes, is nowadays subjected to demanding requirements of environment compliance.

A continuous effort is made in order to implement chemical processes which have a minimum environmental impact and this field of research is known as "green chemistry".

However, the synthesis must satisfy industrial requirements, especially good yields, final purity of the product and plant management.

Aromatic aldehydes are an important category of chemicals which are used for example in pharmaceuticals, cosmetics, food industry, agrochemicals, dyes and plastic additives.

A convenient synthetic route to obtain aromatic aldehydes is represented by the oxidation of the corresponding alcohols or alkenylbenzenes.

In the mainstream of the "green chemistry", photocatalytic oxidation of an alcohol is a convenient way to obtain aldehydes.

Generally, photocatalytic oxidation is used in detoxification of water from organic pollutants (Amat et al., Applied catalysis B: Environmental 73 (2007) 220-226).

Palmisano et al., Adv. Synth. Catal. 2007, 349, 964-970, report the photocatalytic oxidation of 4-methoxybenzyl alcohol to p-anisaldehyde in water with organic-free suspensions of titanium dioxide. The only by-products present were traces of 4-methoxybenzoic acid and aliphatic products, carbon dioxide being the other main oxidation product. The work of Palmisano et coll. aims at investigating the nature of the $TiO_2$ photocatalyst and at their best, the selectivity of p-anisaldehyde is 41.5%.

Augugliaro et al., Photochemical & Photobiological Sciences, 2009, 8, 663-669, and Yurdakal et al., Green Chem. 2009, 11, 510-516, illustrate photocatalytic partial oxidation of 4-methoxybenzyl alcohol to 4-methoxybenzaldehyde in organic-free water suspensions of $TiO_2$ catalysts of different phases with selectivities to p-anisaldehyde up to about 74%. As already observed in other works, the Authors explain that oxidation of the alcohol to the corresponding aldehyde is partly affected by the direct mineralization of the alcohol to $CO_2$ and by overoxidation of the aldehyde to open ring derivatives.

This kind of problem generally can occur with the preparation of aromatic aldehydes by means of oxidation reactions.

There is the evident need to achieve a more accurate control of an oxidation reaction in order to avoid side products which lower the yield of the final product and make more difficult to obtain it in a pure form.

Higashimoto et al., Journal of Catalysis 266 (2009) 279-285, achieve yield of benzaldehyde higher than 95% from benzyl alcohol by carefully selecting the type of $TiO_2$ catalyst. It must be observed, however that the process is carried out in acetonitrile. This solvent is to be abandoned in view of safety and environmental impact.

Other kinds of $TiO_2$ catalysts are disclosed in CN101531575.

However, the problem to achieve an optimal control of the oxidation reaction and good separation of the final product from the reaction media still remains.

Many purification and separation methods are well known to the person of ordinary skill in the art. For example liquid mixtures can be separated by adsorption or distillation, but these methods are affected by high costs, especially in terms of equipment, energy and safety. Moreover, in this specific context of heterogeneous photocatalysis, wherein the catalyst is in an extremely fine powdery form, there is the need to improve separation methods of the liquid product from the catalyst.

Other problems derive from the intrinsic difficulties of operating in a continuous mode.

Pervaporation is a well-known method used for separating liquid mixtures. A liquid mixture is contacted with a non-porous membrane. The compounds in the liquid mixture permeate the membrane and then evaporate downstream. Different solubilities and diffusivities of each compound make the separation possible. Flow is maintained by applying a vacuum downstream or with a carrier gas.

Use of pervaporation is well documented in the art. Membrane technology is disclosed for example in JP58089901, EP0311882, EP0381477. These membranes are used to separate water from alcohols or ketones, but there is no disclosure of separation of an aldehyde from its original reactant.

EP0423949 and EP0584414 disclose non-porous separating membranes used in a pervaporation process to separate an aliphatic alcohol with less than three carbon atoms from oxygenated organic compounds, such as ethers, aldehydes, ketones and esters. Alcohol permeates the membrane, while oxygenated compounds remain in the retentate.

EP1167333 discloses a pervaporation process for removing water from the reaction media in the preparation of acetals and ketals.

Boddeker et al. Journal of Membrane Science 137 (1997) 155-158 disclose the isolation of vanillin from bioconversion broth by means of pervaporation.

WO2009/130245 discloses the use of pervaporation process to partially separate water from a reaction process comprising condensation, dehydration and hydrogenation of ketones and aldehydes.

DE4337231 discloses a process wherein the concentration of formaldehyde is obtained by pervaporation of water through a particular membrane, which is impermeable to the aldehyde.

The problem of separating the aldehyde from its corresponding alcohol, or in general from its corresponding starting compound in an oxidation reaction is not disclosed in the above mentioned references. This problem has been faced, but not solved in satisfactory manner.

An attempt to control oxidation reaction of an alcohol to the homologous aldehyde and at the same time separating the final product is disclosed in Benguergoura et al., Journal of Membrane Science 229 (2004) 107-116. The Authors make essential that oxidation reaction is carried out in anhydrous environment for its control, which is contrary to the purpose of the present invention, which is directed to reactions in aqueous, preferably organic-free media.

Pervaporation is used to separate alcohol from its corresponding aldehyde and this is enabled for n-propanol/n-propanaldehyde and n-butanol/n-butyraldehyde, but the Authors stress out a poor selectivity between alcohol and its corresponding aldehyde. In fact, pervaporation through conventional polydimethylsiloxane (PDMS) is found effective for preventing further oxidation of primary alcohols, however, the overall yield of the reaction, in terms of aldehyde is affected by the simultaneous permeation of the alcohol. The Authors propose to overcome this problem by developing a suitably chemically-designed membrane. Also, the oxidation system is a solution $K_2CrO_7/H_2SO_4$, which is completely different from the photo-oxidation system used in the present invention.

Solovieva et al., Journal of Membrane Science 110 (1996), 253-255 disclose a catalytic process of alcohol oxidation with separation of the final product by pervaporation. However, the experimental results are not very clear. It must be observed that the oxidation reaction is not controlled satisfactorily, since the acids are always formed. The separation mechanism (ion-exchange) is different from the solution-diffusion mechanism usually operating in pervaporation. Furthermore the results are not clear. The membrane seems to be used mainly with the aims to act as a "carrier" for the catalyst (see cited reference 2: "Polymer sulfofluoride films as carriers for metalloporphyrin catalysts") and to obtain a gaseous stream with the aldehydes. It appears obvious that the aldheydes must be largely diluted in the permeate carrier gas, otherwise they cannot permeate and need a further separation stage. From FIG. 2 one cannot understand if the aldheydes are formed at the feed side or inside the polymer, and it is not said which is the fate of the residual reagents and of the side-products. The only clear result is that the "effective oxidation rate constant" is 100 times lower than the one obtained in heterogeneous photocatalysis: "The value is less than k in the case of heterogeneous catalysis by a factor of $10^{-2}$.". On the basis of these results any expert designer would discard this method to utilize the heterogeneous photocatalysis with a possible post reaction separation.

The prior art provides information only for short-chain linear aliphatic alcohol/aldehyde series. That information cannot be transferred to aromatic series.

Kanani et al., Ind. Chem. Res. 2003, 42, 6924-6932 study recovery of tea aroma components by pervaporation technique. This work reports separation factors for binary and multicomponent mixtures. Although separation factors are acceptable in tea extract, when measured in binary or multicomponent situation, they are not very good. Moreover, Kanani et al. show the behaviour of phenylacetaldehyde and benzyl alcohol, which is not a corresponding couple, hence cannot be used as predictable model for the oxidation reaction. The skilled person would not find any successful indication.

She et al., Journal of Membrane Science, 271 (2006) 16-28 dissert on a theoretical basis about the separation factors in pervaporation of flavour organics. They conclude that interaction effects among different components are usually not relevant and remain substantially the same both in a binary (water/compound) and a multicomponent mixture. Also in this case, there are no data on a corresponding alcohol/aldehyde couple, so that this paper cannot be used to make any prediction.

Camera-Roda and Santarelli, Journal of Solar Energy Engineering, February 2007, 129, 68-73 discuss intensification of water detoxification by integrating photocatalysis and pervaporation. As far it is known to the present inventors, this is the only piece of prior art combining photocatalytic oxidation and pervaporation. However, this work aims to a different goal than the one of the present invention. Actually, the reaction oxidation of an aromatic alcohol is enhanced as much as possible to mineralization, namely to $CO_2$, and no control of the reaction is envisaged.

The mechanism also is different. In fact photocatalysis is utilized to transform a poorly permeating compound (4-chlorophenol) into other much more permeable intermediate compounds. So, in this "detoxification", with aims that are clearly very different from those of a chemical synthesis, intermediate compounds pervaporate faster than the original pollutant and concurrently it is not necessary that photocatalysis complete their mineralization.

Therefore, the state of the art does not provide any guidance on how to achieve the accurate control of the oxidation of an aromatic alcohol to the corresponding aldehyde in a photocatalytic non-organic, aqueous environment.

SUMMARY OF THE INVENTION

It has now surprisingly been found that the combination of oxidation of an aromatic compound to its corresponding aldehyde with simultaneous pervaporation of the obtained aldehyde allows a good control of the oxidation reaction, without substantial generation of aldehyde oxidation side products and good yields and purity of the desired aldehyde.

With the integrated process thus obtained, the selectivity can be maintained at any time close to the highest value achievable with a given photocatalyst. This value without pervaporation can be obtained only at the beginning of the process with a conversion value close to zero, which clearly cannot be a possible operating value. At longer times, without the separation process, the subsequent reaction of degradation of the aldehyde has the effect of decreasing the selectivity. As a consequence, the yield (given by the product of the selectivity by the conversion) with the pervaporation (PV) can be always increased with time and at any time it is higher than the one achieved without PV.

Therefore, it is an object of the present invention a process for the preparation of an aromatic aldehyde by means of the oxidation of the corresponding compound in aqueous medium and separation of said aldehyde from said medium by pervaporation.

Another object of the present invention is the use of a pervaporation membrane in the above process.

A further object of the present invention is a plant to carry out the above process.

These and other objects will be illustrated in the foregoing also by means of Figures and Examples.

FIG. 6 shows the amounts of alcohol (a) and (b) in the retentate and cumulatively collected in the permeate. Same experiment FIG. 5 refers to.

FIG. 7 shows conversion, selectivity and yield in the same experiment FIG. 5 refers to.

DETAILED DESCRIPTION OF THE INVENTION

Figure 1:
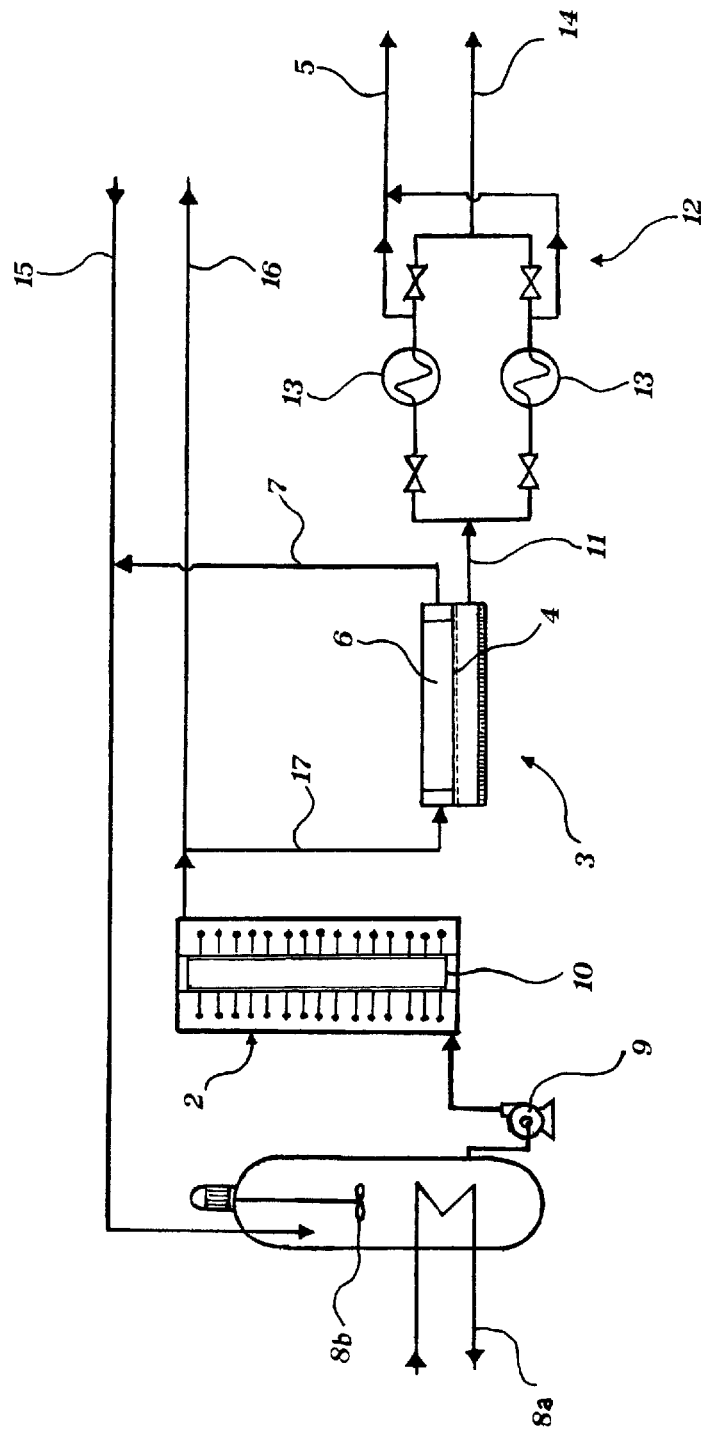
FIG. 1 shows an exemplary apparatus to carry out the process of the present invention.

With initial reference to FIG. 1, a plant for the production of aromatic aldehyde according to the process of the invention is indicated, as a whole, with the numeral reference 1.

The plant 1 comprises a reactor 2, so arranged as to perform an oxidation reaction in a suitable aqueous reaction medium, which is connected downstream to a pervaporation unit 3 for separating from the reaction medium an aromatic aldehyde obtained from the reaction occurred in the reactor 2.

The pervaporation unit includes a suitable membrane 4 which is put in contact with the reaction medium coming from the reactor 2. The membrane 4 is selectively permeable so that a permeate flux 5 and a separate retentate flux 6 are formed downstream the pervaporation unit 3.

Flow moving means, comprising a pump 9, are provided in plant 1 in order to move the reaction medium through the reactor 2, downstream to the pervaporation unit 3 and through this latter. Flow moving means are designed and operated so that an actual coupling (integration) of the two steps of the process, reaction and membrane separation, is established and a "simultaneous" process instead of a sequential operation is obtained.

In general, two or more steps of a process are defined "simultaneous" (or, alternatively, "integrated") when the residence time of the reaction medium in such steps is much lower than the characteristic time of disappearance of the main reactant from the system. In this way, a substantially perfect mixing is obtained throughout the system, so that the concentration of every compound at a predetermined time is uniform, and independent on the specific sampling point of plant 1.

As a consequence, each part of the plant operates on a reaction medium having the same concentration, as if the respective process steps were provided in one single plant unit, whereas, they are actually separated.

In particular, in the present description and claims, reaction and membrane separation, are defined "simultaneous" when the ratio between the residence times of the reaction medium both in the reactor 2 as well as in the pervaporation unit 3, and the characteristic time of disappearance of the main reactant (which ideally should approach 0) is equal to or lower than 0.1, preferably equal to or lower than 0.01. The characteristic time of disappearance of the main reactant may be established in different ways. A conservative method for its determination, defines the characteristic time of disappearance of the reactant as the derivative of its concentration C with respect to time t at time t=0, divided by the reactant concentration $C_0$ at time t=0.

In a preferred embodiment, the process according to the present invention is carried out in way, wherein the ratio between the residence times of the said medium both in a reactor, wherein said oxidation is carried out, as well as in a pervaporation unit, wherein said pervaporation occurs, and the characteristic time of disappearance of the said corresponding starting compound is equal to or lower than 0.1, more preferably said ratio is equal or lower than 0.01.

In the preferred embodiment of the invention here disclosed, the retentate flux 6 is then recycled into the reactor 2 by means of a recycling line 7, so as to recover the unreacted reaction medium.

In the recycling line 7 is also inserted a feeding tank 8, which is suitably equipped with heating means 8a and mixing means 8b, and which is connected to the reactor 2 by means of the pump 9.

Preferably, the reaction carried out in the reactor 2 is a photo-catalytic oxidation.

The reactor 2 is any kind of reactor suitable for the purpose, such as for example an annular reactor, and, to this end, radiating means, such as a UV lamp 10 installed inside the reactor 2, may be associated with the reactor 2 in order to allow the photo-oxidation to occur. Alternatively, the reactor 2 can be designed in such a way to receive a suitable amount of radiation from an outside source, which may be constituted by artificial radiating means or by sunlight.

Examples of this kind of reactor are well known in the art, as disclosed for example in the references mentioned in this application.

Analogously, pervaporation unit is well-known in the art and examples are shown in the above mentioned references.

The pervaporation unit 3 can be designed in different ways, in view of the plant necessities, to contain at least one pervaporation cell module equipped with the membrane 4. Commercial modules are suitable to the purposes of the present invention, such as, for example the PERVAP® modules marketed by Sulzer.

The permeate flux 5 coming out from the pervaporation unit 3 is transferred, under vacuum conditions, through a line 11 to a collecting unit 12, equipped with liquid nitrogen traps 13 in order to recover the desired product from the incondensables compounds which are sucked away by the vacuum pumps through line 14.

As an alternative, to the liquid nitrogen traps 13 any other equivalent conventional means may be used. An optional feed line 15 may be connected to the recycling line 7 for introducing, when appropriate, fresh reaction medium. As an alternative, the feed line 15 may be opened directly into the feeding tank 8.

Furthermore, an optional purge line 16 may be provided downstream the reactor 2, in order to avoid the accumulation in the reaction medium of non-permeable and non-reactive compounds. The purge line 16 may be provided in a line 17 connecting the reactor 2 to the pervaporation unit 3.

In particular, a combination of a photocatalytic reactor and a pervaporation unit can be seen in the above mentioned Camera-Roda and Santarelli, Journal of Solar Energy Engineering, February 2007, 129, 68-73.

The process of the invention is put into effect by operating the plant 1 as follows.

Briefly, the feeding tank 8 is fed through the feed line 15 with the starting reaction medium which is formed by an aqueous solution of the starting compound with dissolved oxygen, which in photocatalysis has the tasks to replace the oxygen consumed by the oxidation and to act as electron scavenger, as well as the photocatalyst. The latter, as an alternative of being in free form in the reaction mixture (slurry), may be provided in form of a fixed bed.

In the feeding tank 8, the reaction medium is properly heated and mixed and, thanks to the action of the pump 9, the same is recycled along the reactor 2, the pervaporation unit 3 and the recycling line 7. When deemed appropriate, radiating means are turned on and the reaction of photo-oxidation takes place in the reaction medium flowing through reactor 2. Recycling flow is adjusted according to reaction and plant conditions and this adjustment is well within the knowledge of the person of ordinary skill in the art.

The reaction medium is then transferred to the pervaporation unit 3 along line 17, where some compounds, among which the aromatic aldehyde, are separated from the reaction medium in the permeate flux 5. The retentate flux 6 is then recycled through the recycling line 7 to the feeding tank 8.

In a most preferred way, plant 1 is so operated, for instance designing and controlling properly pump 9, as to obtain a high recycle ratio.

In particular, the flow of the reaction medium through plant 1 is such that its residence times in the reactor 2 as well as in the pervaporation unit 3 are equal or lower than $1/10$, preferably equal or lower than $1/100$, with respect to the characteristic time of disappearance of the main reactant from the system, thus assuring the perfect mixing of the reaction medium throughout the plant.

According to the present invention, the desired aldehyde goes through the pervaporation membrane (permeate), while the unreacted starting compound, corresponding to the desired aldehyde is retained in the aqueous reaction medium (retentate).

According to this embodiment, the unreacted starting compound corresponding to the desired aldehyde is recycled to the reactor.

The present invention relates to a process for the preparation of aromatic aldehydes from a corresponding starting compound. The advantage provided by the process of the present invention is an accurate control of oxidation reaction of the starting compound (typically an alcohol) to the desired corresponding aldehyde, in order to avoid further oxidation and the consequent presence of undesired side products, such as the corresponding carboxylic acid, carboxylic ester with the starting compound, mineralization of the reactants to carbon dioxide and other side reactions, such as opening of the aromatic ring. A further advantage of the present invention is in the efficient separation of the desired aldehyde from the corresponding starting compound and the possibility of recycling the starting compound in a semi-continuous or continuous process.

Also the apparatus according to the present invention can be designed for a semi-continuous or continuous process. The person of ordinary skill in the art can arrange the apparatus herein described just resorting to the common knowledge and further explanations are no needed herein.

In one embodiment of the present invention, the integration of photocatalysis and pervaporation (simultaneous process) has been achieved with the coupling of the two steps of the process by the recirculation in a closed loop of the retentate from the pervaporation modules into the reactor and back to pervaporation, according to the scheme in FIG. 1 without the optional feed and purge streams. The permeate is collected by condensation of the "pervaporated" vapours and represents the product stream. If the flow rate is sufficiently high to get a residence time in the reactor and in the pervaporation modules much shorter than the characteristic time of disappearance of the corresponding starting compound (alcohol) from the system, the coupling is almost complete and the system behaves as a batch.

In another embodiment of the present invention, a feed is continuously introduced into the system with a flow rate equal to the sum of the flow rates of the permeate and of the purge stream, after a transient time, the system can work in a (semi) continuous mode approaching the behaviour of a CSTR reactor (Continuous Stirred Tank Reactor). In this latter case, an "overall mean residence time", defined as the mean time spent by fresh feed in the CSTR-like system (or in a component thereof) before going out of the system can be calculated dividing the volume of the CSTR-like system (or of the component thereof) by the volumetric flow rate of the fresh feed.

Different types of reactors have been used, e.g. slurry reactors or fixed bed reactors with various dimensions and configurations or with different light sources, but the results were qualitatively the same and the same phenomena were observed.

Any kind of aromatic compound can be used in the present invention as starting material for the preparation of the corresponding aromatic aldehyde. As intended in the context of the present invention, "aromatic aldehyde" means a compound having at least one CHO group, which can be directly linked to an aromatic ring or connected to said aromatic ring by a carbon chain. Although the length of the carbon chain may not be critical, it will usually be up to six carbon atoms. The aromatic ring can be mono- or polycyclic and can be substituted in any of its available positions with other chemical groups, with the condition that these groups do not interfere with the oxidation reaction.

Accordingly, as intended in the context of the present invention, a "corresponding starting compound" is a compound having an aromatic ring carrying a functional group which can be oxidized to the formyl group, thus giving the desired aromatic aldehyde. A first preferred starting compound is a primary aryl aliphatic alcohol, in particular a derivative of an aryl alkanol, more preferably a benzyl alcohol. Although the length of the carbon chain of the alkanoyl may not be critical, it will usually be up to six carbon atoms. Examples of such alcohol are benzyl alcohol, 4-methoxybenzyl alcohol, 4-hydroxy-3-methoxybenzyl alcohol, 4-nitrobenzyl alcohol, 4-methylbenzyl alcohol, 4-(trifluoro)methylbenzyl alcohol, 4-tertiarybutylbenzyl alcohol, 4-hydroxylbenzyl alcohol, 2-phenylethanol. A second preferred compound is an alkenylbenzene. Although the length of the alkenyl carbon chain may not be critical, it will usually be up to six carbon atoms. Examples of said alkenyl benzene are 4-allyl-2-methoxy phenol (eugenol), 2-methoxy-4-(1-propenyl)phenol (isoeugenol), hydroxylated alkenyl aromatics, (E)-3-(4-hydroxy-3-methoxy-phenyl)prop-2-enoic acid (ferulic acid).

In a first preferred embodiment, the process of the present invention is applied to the couple benzyl alcohol/benzaldehyde or the couple 4-methoxybenzyl alcohol/4-methoxybenzaldehyde (anisaldehyde).

In another preferred embodiment, the process of the present invention is applied to the couple (E)-3-(4-hydroxy-3-methoxy-phenyl)prop-2-enoic acid (ferulic acid)/4-hydroxy-3-methoxybenzaldehyde, also known with the name of vanillin, which is the most utilized aroma in the food, cosmetic, pharmaceutical and nutraceutical industries.

In principle, any kind of oxidation can be carried out in the aqueous medium. Examples of oxidation are with chemical oxidants, microbial agents and photo-oxidation.

The first preferred embodiment is catalytic photo-oxidation (also known as photocatalytic oxidation).

The usual concentration of the reagents is relatively low both in photocatalysis and in pervaporation. As a rule of thumb, the concentration can vary from 0.01 to 100 mmol/L, preferably from 0.01 to 50, more preferably from 0.05 to 50, even more preferably from 0.1 to 10. More often an upper limit is given by the limited aqueous solubility of the original reactants. These relatively low values of concentration usually are not a problem for the product, since they could represent acceptable values for aromatic substances or can be easily increased by conventional techniques.

Opposite effects of the temperature have been observed on the photocatalysis rate and on the pervaporation rate. The increase of the temperature causes a significant increase of the pervaporation flux (the separation factor changes only slightly), but a decrease of the reaction rate, probably due to the reduced dissolved oxygen content. However the effect on the pervaporation flux is more important. So, even if it is possible to work at whatever temperature from ambient temperature to 70° C., it is probably preferred to operate close to the higher value, say 60-65° C. Anyway the upper limit of the temperature is given by the thermal resistance of the membrane or by the boiling point of the reacting solution or by the thermal degradation of the compounds. The first can be augmented by using inorganic membranes, the second by operating at higher pressure. The membranes have been tested for relatively long times at 60° C., with no deterioration.

Different kinds of catalysts can be used in the process of the present invention.

The catalyst can be used in different forms, such as suspended in aqueous medium, in a slurry, or immobilized, in fluid or fixed bed.

In the preferred embodiment of catalytic photo-oxidation, conventional catalysts can be used. Examples can be found in the cited references and in WO2007002614. A preferred catalyst is titanium dioxide ($TiO_2$). Many forms of $TiO_2$ are available for the purpose of the present invention. Commercial photocatalytic powders, such as for example Aeroxide P25, Merck $TiO_2$, Hombikat UV100, Sigma Aldrich, can be used. Otherwise home-prepared photocatalytic powders or immobilized films can also be utilized (the $TiO_2$ precursors can be various organometallic or inorganic titanium compounds). For example, as described in the above mentioned references. Amounts of catalyst to be used in the reaction are conventionally as those used in the art.

Pervaporation membranes are commercially available and different kinds are also disclosed in the above mentioned references. It is essential that the membrane is organophilic. A preferred membrane is made of polyoctylmethyl siloxane (POMS) or polydimethyl siloxane (PDMS) which are commercially available by many suppliers, such as for example GKSS.

The membranes which can be used in the present invention are organophilic membranes. In particular, the selective layer can be selected from POMS (polyoctylmethylsiloxane), PDMS (polydimethylsiloxane), PEBA (polyether block amide), PTMSP (polytrimethylsilylpropyne), which, can optionally be loaded with fillers. Generally, fillers are zeolites in the form of fine powders, mainly of the silicalite class, such as ZSM5 or others. With these latter materials, also inorganic membranes can be prepared.

Furthermore, in the case that the photocatalyst is present in the slurry recirculation loop as suspended nano or micro powders, the powders do not pass the membrane and the product stream is always powder-free. In the long series of experiments it has been observed also that the presence of the powders does not affect the performance of the membrane and both the transmembrane flux and the separation factor do not change for fouling even at very long times. It is likely that the possible deposition of photocatalyst powders onto the membrane surface contributes only at a negligible extent to the overall resistance to the permeation, which in a dense membrane is intrinsically rather high even in absence of fouling. It has been experimentally verified that the membranes can withstand for very long times pervaporation with photocatalysis without any appreciable decay of the performances.

An important advantage provided by the present invention is that the process limits the presence of intermediate compounds in the reactor, therefore reaction rate is enhanced. This is due to the fact that the intermediates, if formed, would compete with the starting compound for the active sites or the photogenerated oxidizing agents.

The parameter R is defined as $R=k_d*V/(J*A)$, wherein $k_d$ is the constant of disappearance of the original reactant, which can be evaluated, for example at the starting time, when other compounds are not yet present, V is reactor volume, J is the volumetric flow of permeate (for example L/(h m$^2$); A is membrane area.

The following examples further illustrate the invention.

Example 1

A simplified model of continuous process according to FIG. 1 and working in steady state shows the effect of R.

The process is directed to the oxidation reaction of 4-methoxybenzyl alcohol (MBA) to obtain 4-methoxybenzaldehyde (MBAD).

The calculated characteristic time of disappearance of MBA is 3.58 h and the process is considered simultaneous. In other words, the pump 9 is so operated that the ratio between the residence times of the reaction medium in the reactor 2 and in the pervaporation unit 3 (when present), for each loop of the reaction medium in the plant, and the characteristic time of disappearance of MBA is well below 0.01.

Further simulations have shown that results in terms of selectivity, yield and conversion are not dependent from the specific value of the above ratio, provided that the same is lower than 0.1.

Figure 8:
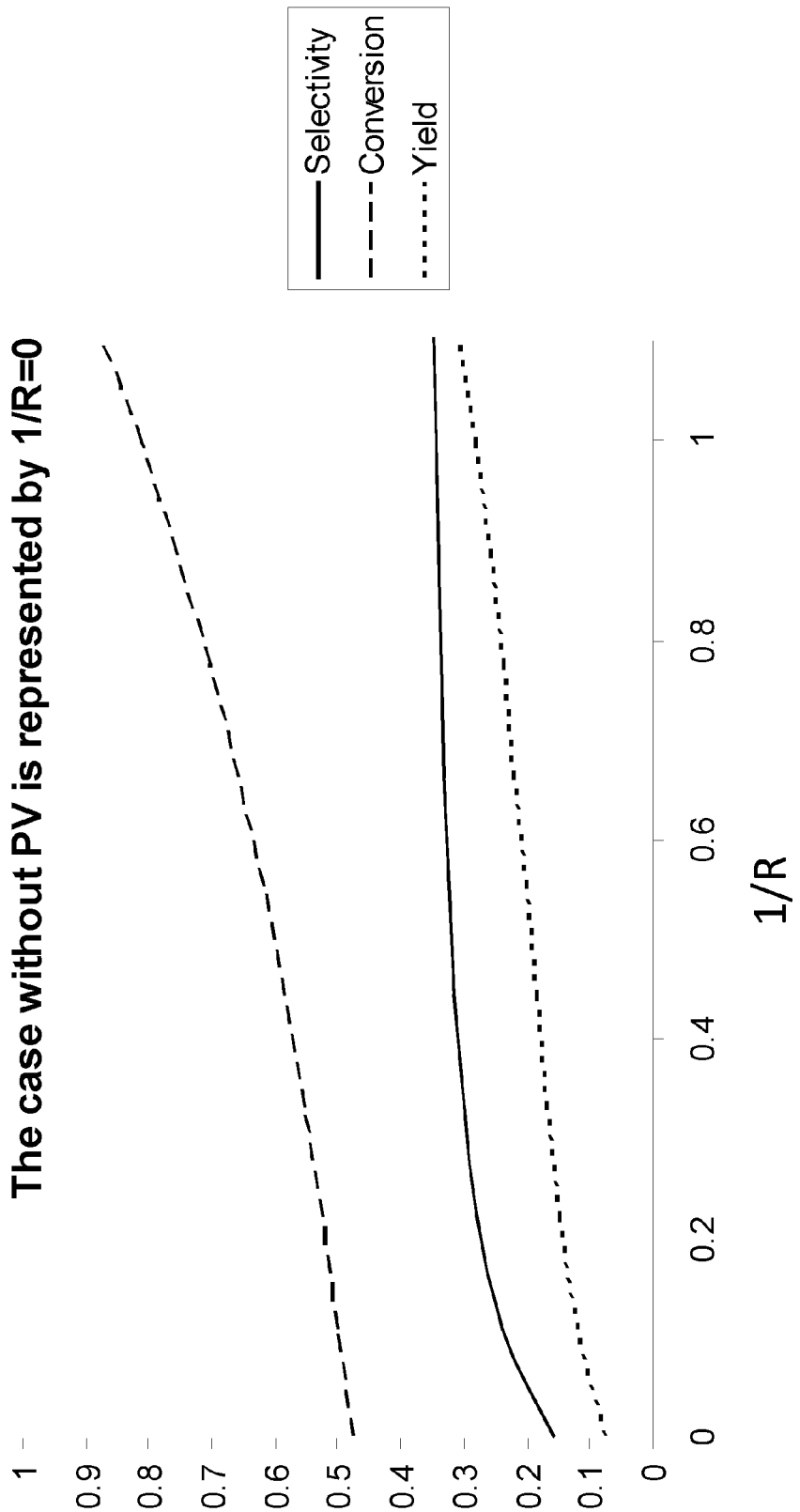
FIG. 8 shows the effect of a change of the membrane area (the area is inversely proportional to R) in a continuous process. Volume of the reactor=0.5 L, volumetric flow rate of the feed=0.05 L/h, conventional residence time=10 h.

FIG. 8 shows that an increase of A allows to obtain higher values of the selectivity. The maximum operating value of 1/R (that is of the membrane area) is limited by the feed flow rate, since the membrane area must give a permeate flow rate smaller than the feed flow rate, otherwise the purge is depleted and the same compounds accumulate in the reactor.

A rough estimate of the parameters for the experiment without PV, whose results are plotted in FIG. 8, shows that in order to work with a value of 1/R=1, the experiment would be carried out with a membrane area of approximately 0.45 m$^2$. This means that with that photocatalytic reactor the conditions to operate at R=1 imply to use approximately 1 m$^2$ of membrane per 1 L of reactor. Note that the change of volume must be made by increasing the length of the reactor and keeping constant the thickness of the reactor and the concentration of the photocatalyst, in order to keep constant the optical thickness, the parameter that mainly determines the effectiveness of utilization of the light in the reactor.

In this case for a reactor volume of 0.5 L, with a feed concentration of the alcohol=10 mM and a volumetric flow rate of the feed of 0.05 L/h (for an overall mean residence time of the fresh feed in the reactor defined as the ratio between the reactor of the volume and the feed volumetric flow rate of 0.5/0.05=10 h), one obtains:

|  | Integrated process (A = 0.45 m$^2$) | Without PV |
|---|---|---|
| Conversion | 0.81 | 0.47 |
| Selectivity | 0.35 | 0.16 |
| Yield | 0.28 | 0.074 |
| Permeate flow rate L/h | 0.045 | — |
| Purge flow rate L/h | 0.005 | 0.5 |
| MBAD concentration in the permeate mM | 3.1 | — |
| MBAD concentration in the purge mM | 0.19 | 0.73 |
| MBA concentration in the permeate mM | 1.1 | — |
| MBA concentration in the purge mM | 9.0 | 5.26 |
| MBAD in the permeate/MBAD in the purge | 149 | — |
| MBA in the permeate/MBA in the purge | 1.15 | — |

MBAD = 4-methoxybenzaldehyde
MBA = 4-methoxybenzyl alcohol

It must be noted that the reactor without PV could not work in optimal conditions; in fact it is known that a maximum is reached for the yield at an optimal value of the overall mean residence time. So it should be verified if the optimal overall mean residence time is about 10 h.

Figure 9:
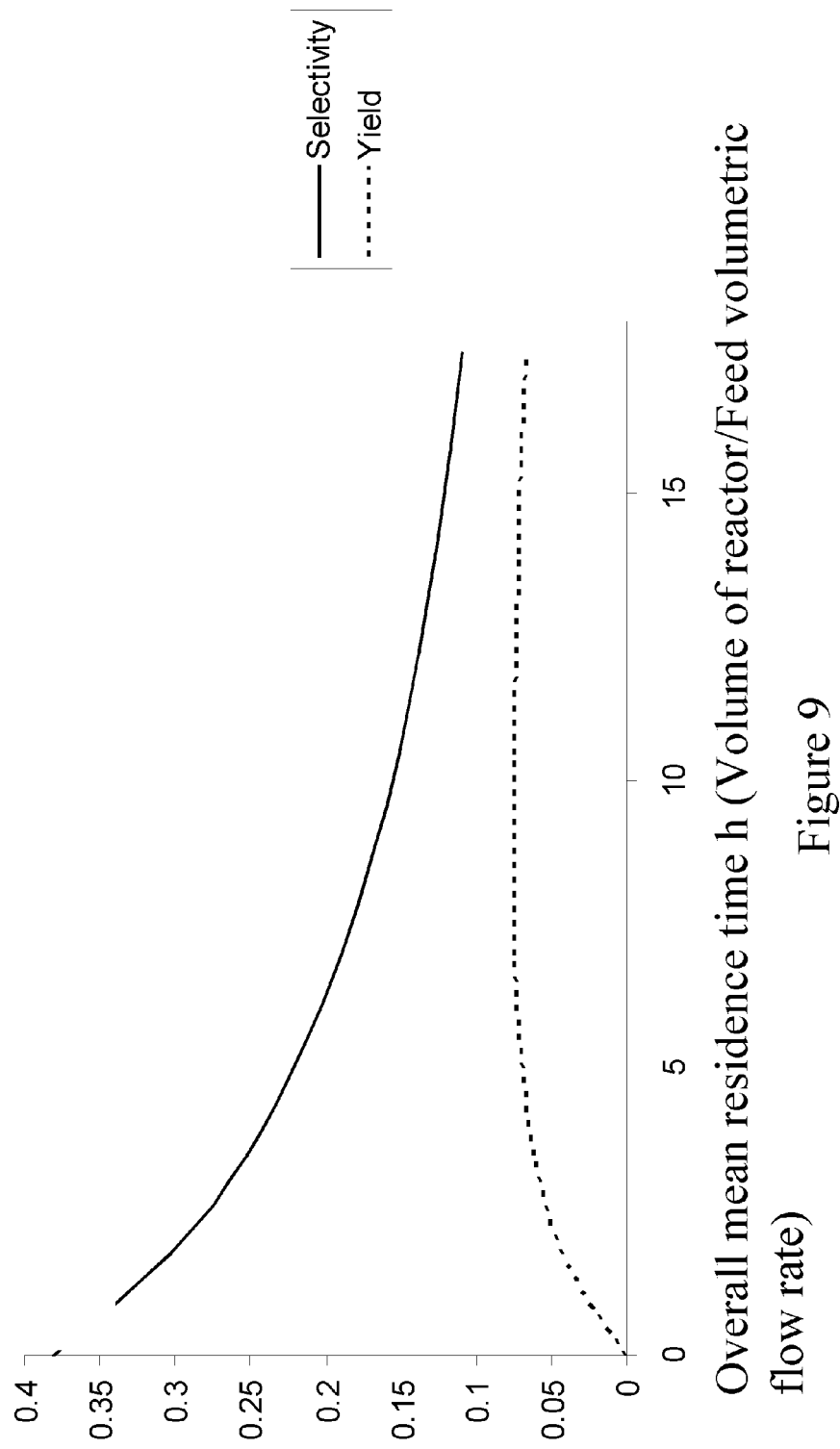
FIG. 9 shows yield and selectivity vs. the conventional residence time (volumetric flow rate of the feed=0.05 L/h) without PV.

This effect is investigated in the following FIGS. 9 and 10.

The typical maximum of the yield is present at about 9 h. Note also the important decrease of the selectivity with the time as a consequence of the consecutive reaction of oxidation of the aldehyde.

Figure 10:
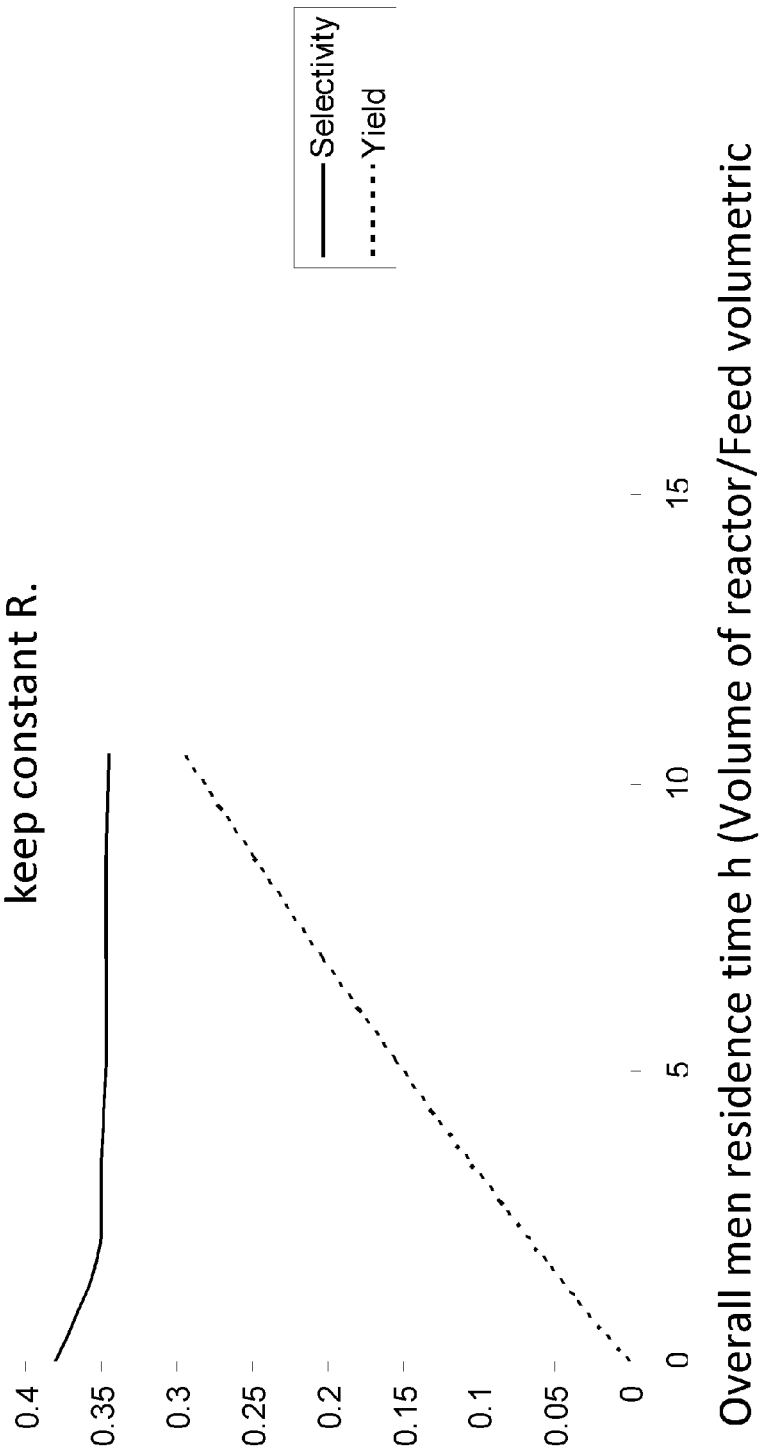
FIG. 10 shows yield and selectivity vs. the conventional residence time (volumetric flow rate of the feed=0.05 L/h) with PV. Membrane area increases proportionally to the conventional residence time to keep constant R.

In FIG. 10 the same simulation is made for the integrated process. In this case the value of R has been kept constant. The constancy of R implies that, when the reactor volume is varied to change the overall mean residence time (the feed volumetric flow rate is fixed at 0.05 L/h), also the membrane area is proportionally increased.

It can be observed that the selectivity is almost independent on the overall mean residence time and the yield is monotonically increasing with the overall mean residence time. However it must be taken into account that also the fixed costs are increasing since they depend on the size (volume of the reactor and membrane area) of the apparatus. The maximum overall mean residence time that can be used (with R=1 and a volumetric flow rate of the feed=0.05 L/h) is about 10.5 h; beyond this value, obtained by increasing the volume of the reactor and concurrently the membrane area, all the flow exits with the permeate stream and the system cannot reach steady state conditions.

Figure 11:
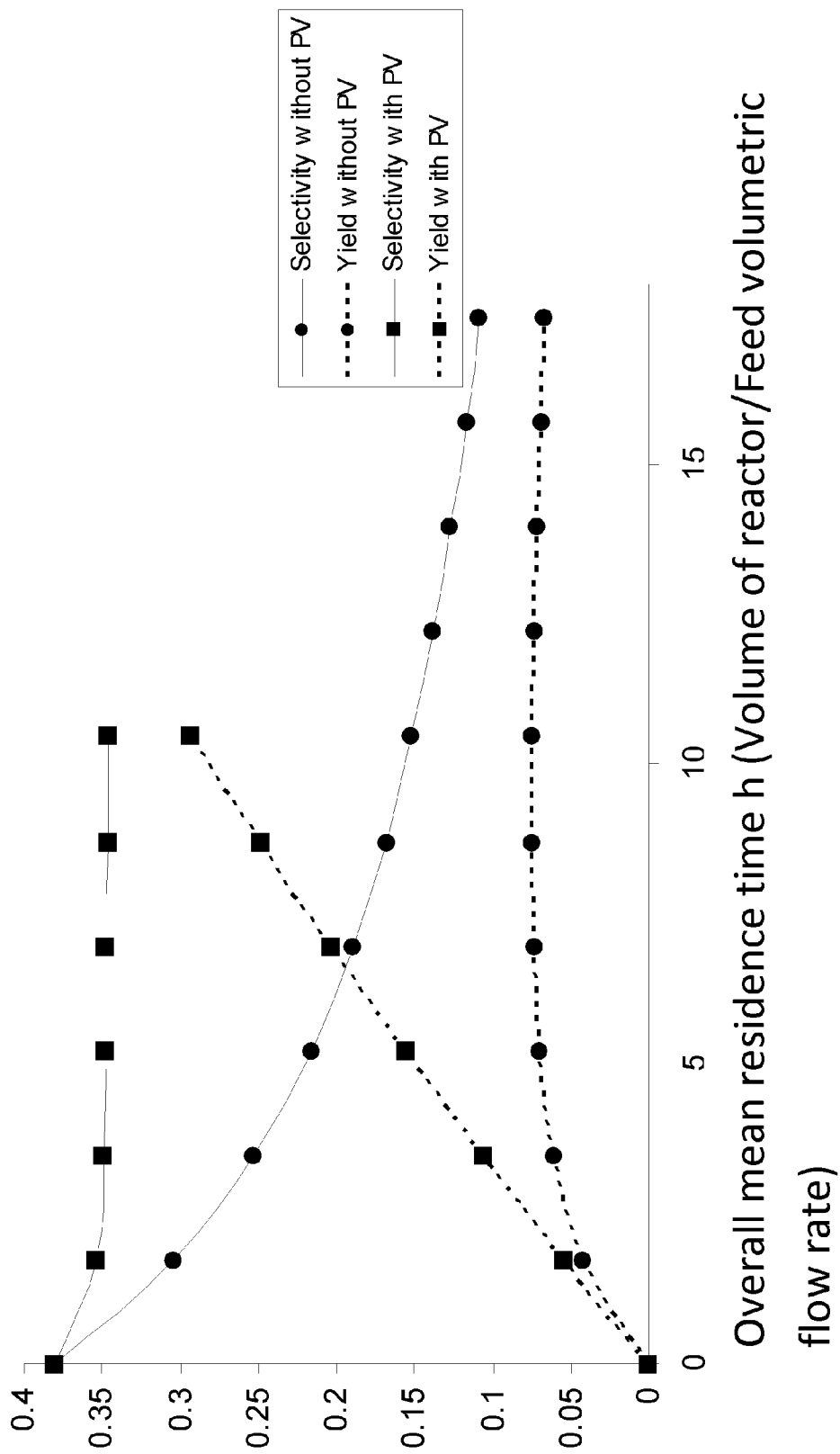
FIG. 11 shows yield and selectivity of the process of the present invention in comparison with the same process without pervaporation step.

The FIG. 11 compares the behaviour of the two different processes.

Example 2

Figure 2:
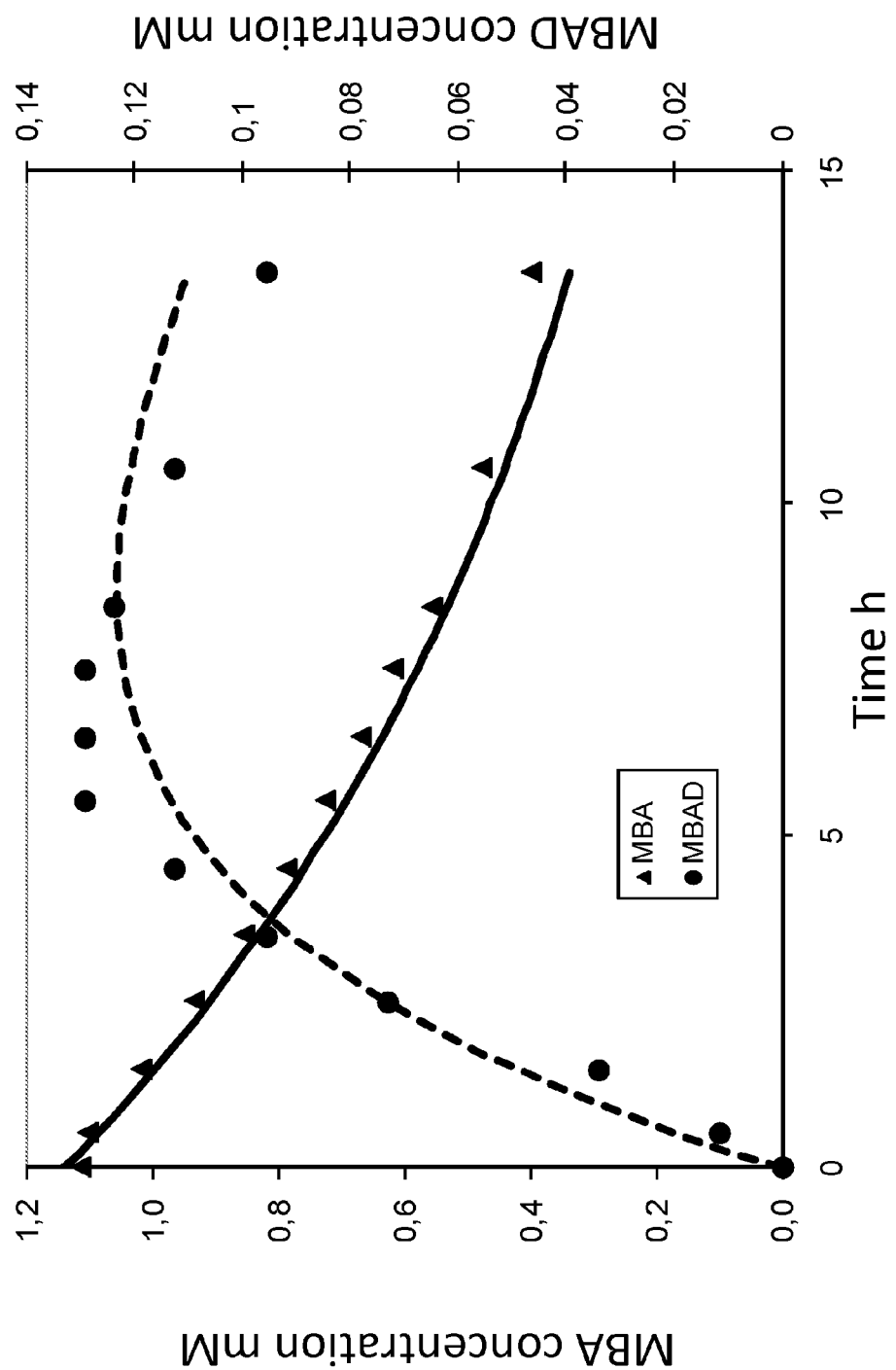
FIG. 2 shows concentration profiles of alcohol and aldehyde, plotted vs. time in a typical photocatalytic experiment.

The consecutive reaction of degradation of the aldehydes in the presence of the activated photocatalyst is confirmed by the occurrence of the characteristic maximum of the concentration at a certain reaction time, as it is apparent in FIG. 2, where the concentration profiles of alcohol and aldehydes are plotted vs. time in a typical photocatalytic experiment (Catalyst, TiO$_2$ Merck, reactor volume 0.5 L, irradiation 125 W medium pressure Hg lamp).

Example 3

Figure 3A:
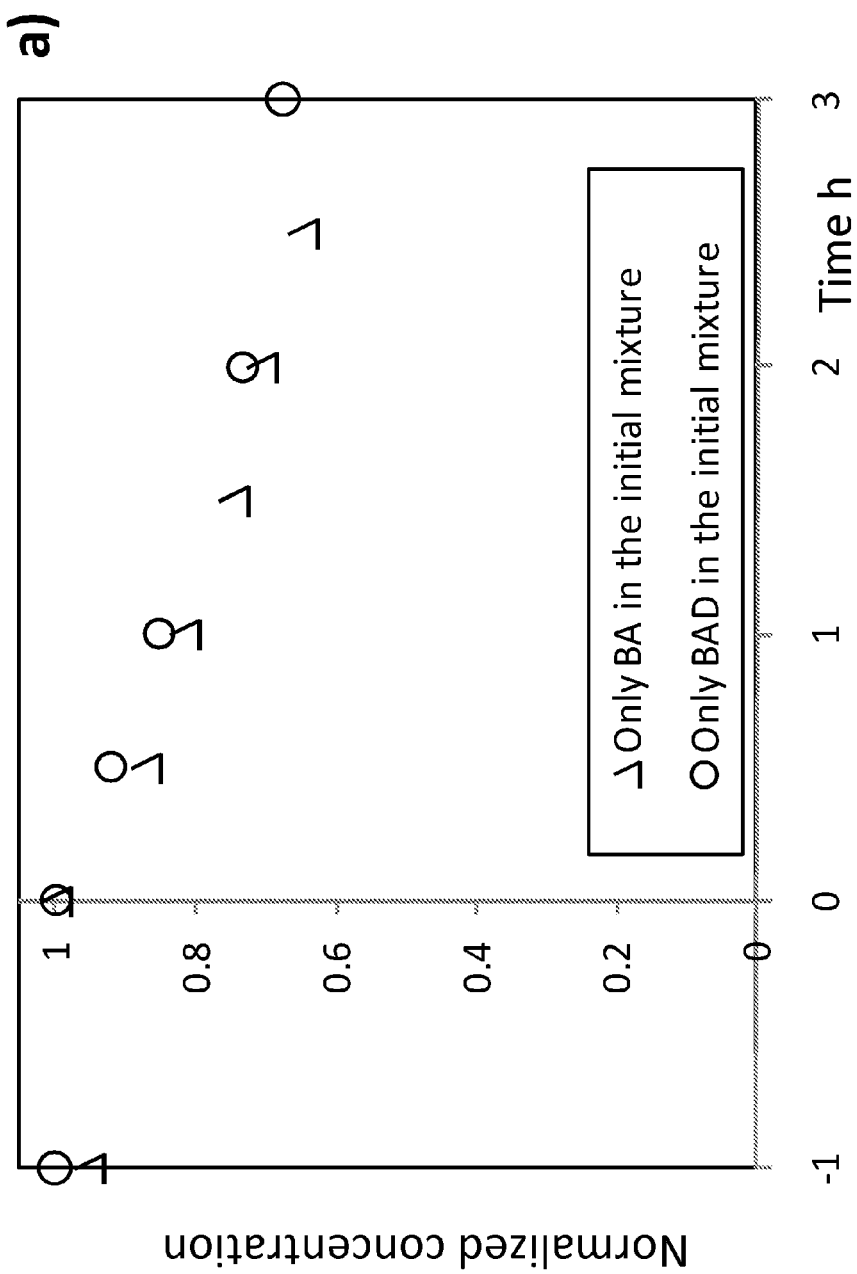
FIG. 3 shows the disappearance of BA and BAD (a) and MBA and MBAD (b) in runs with only the alcohol or only the aldehyde in the initial mixture. Note that the light is switched on at time 0.
Figure 3B:
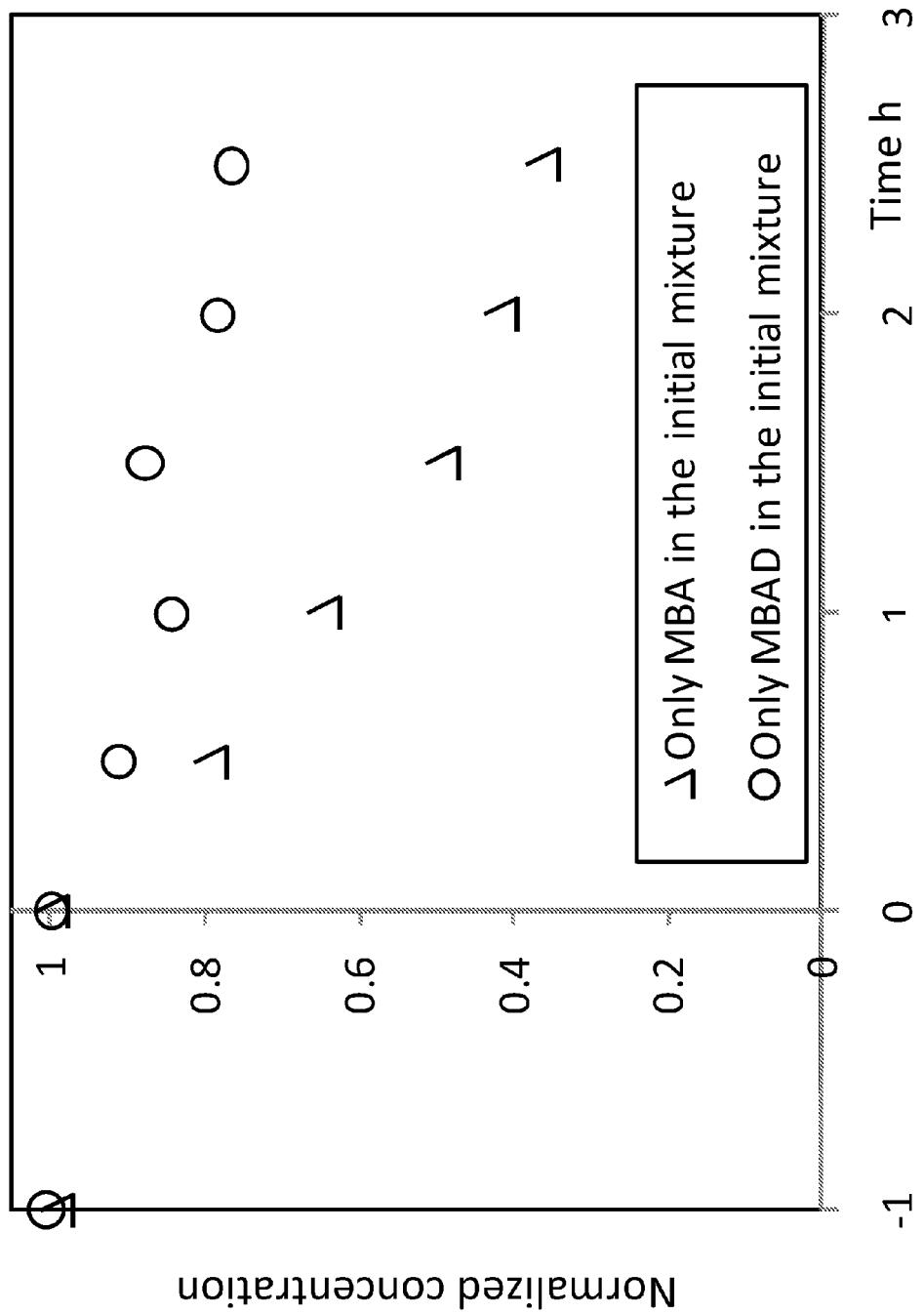

On the other hand, the destruction of the aldehyde is clearly observed also in photocatalytic experiments with the presence of only the aldehyde in the initial mixture. In FIGS. 3a and 3b the time evolution of the concentration of the aldehydes is compared with the one of the alcohols in two different experiments with only the alcohol or only the aldehyde in the initial mixture. The evident decrease of aldehyde concentration shows that also the aldehyde is degraded by photocatalysis. These experiments have been carried out in an annular photocatalytic reactor, with the following characteristics: a Philips TL/08 blacklight 8 W lamp on the axis, internal diameter of the annulus=2.4 cm, external diameter of the annulus=4.2 cm, length of the illuminated zone=27.5 cm, catalyst Aeroxide P25 at a concentration of 0.5 g/L, complete recycle of the slurry by a peristaltic pump at a flow rate of 80 L/h, initial concentration of the reactants about 1 mM, total volume of the slurry=1.3 L, temperature=40° C. The slurry was ultrasonicated for 15 min before the introduction into the reactor.

Example 4

Figure 4:
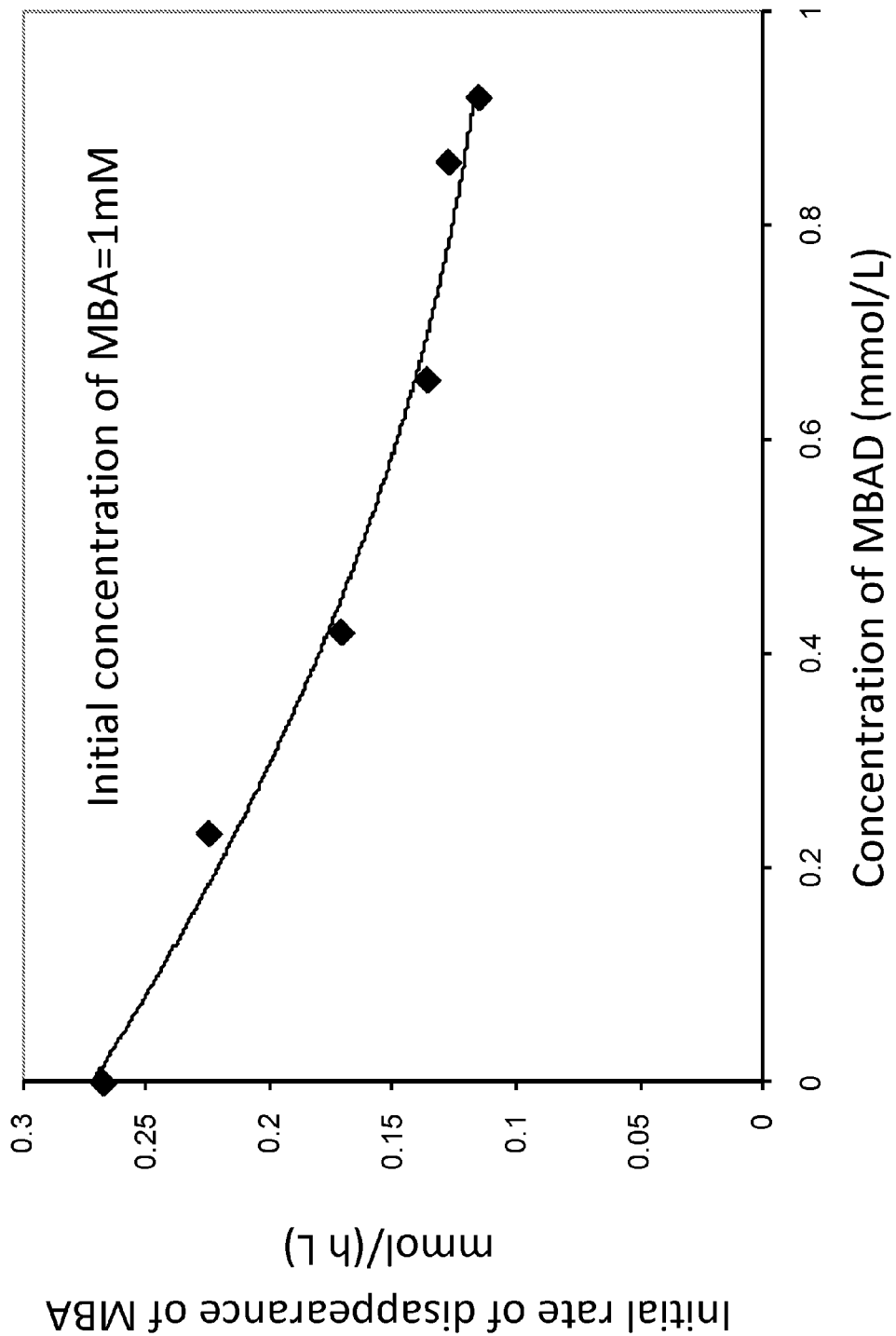
FIG. 4 shows the initial rate of disappearance of the original mother compound (MBA) as a function of the initial content of the aldehyde (MBDA).

The presence of the aldehyde in the mixture in contact with the photocatalyst can be detrimental also because the aldehyde is competitive with the starting compound (the alcohol) for the active sites and the photogenerated oxidizing agents, so that it slows down the rate of oxidation of the alcohol. A clear confirmation of this phenomenon can be obtained by varying in the initial mixture the concentration of the aldehyde, but keeping constant the concentration of the alcohol. The results, obtained at the same previous experimental conditions except the initial concentrations of the compounds, are plotted in FIG. 4, where it is apparent that the aldehyde can significantly hinder the rate of oxidation of the alcohol.

In order to characterize the membranes and to determine the separation properties, the flux and the separation factor of the organophilic pervaporation membranes have been measured in normal pervaporation tests.

A stainless steel module holds a flat sheet of the membrane with an active surface of 160 cm$^2$. The cross section for the passage of the fluid is 2 mm thick and 10 cm wide and the length of the active zone of the membrane is 16 cm, with a flow rate of 80 L/h.

The permeate is maintained at 5-10 mbar and the vapours are collected by condensation in a liquid nitrogen trap. In table I, the separation factors, $\alpha_{i,j}$, of compound i in comparison with compound j, and the fluxes at different conditions are reported.

TABLE I

Pervaporation performances of (POMS/PEI) GKSS membrane.

| Feed composition (Values of concentration in mM) | $\alpha_{alcohol, water}$ | $\alpha_{aldehyde, water}$ | $\alpha_{aldehyde, alcohol}$ | Flux kg/(hm$^2$) | Temperature ° C. |
|---|---|---|---|---|---|
| [BA] = 1.5 [BAD] = 0.1 | 17 | 224 | 13 | 0.14 | 60 |
| [MBAD] = 0.28 | — | 18 | — | 0.09 | 40 |
| [MBA] = 1.35 | 0.11 | — | — | 0.11 | 40 |

TABLE I-continued

Pervaporation performances of (POMS/PEI) GKSS membrane.

| Feed composition (Values of concentration in mM) | $\alpha_{alcohol, water}$ | $\alpha_{aldehyde, water}$ | $\alpha_{aldehyde, alcohol}$ | Flux kg/(hm$^2$) | Temperature °C. |
|---|---|---|---|---|---|
| [MBA] = 1.3<br>[MBAD] = 0.21 | 0.12 | 16 | 130 | 0.11 | 40 |

MBAD = 4-methoxybenzaldehyde
MBA = 4-methoxybenzyl alcohol
BAD = benzaldehyde
BA = benzyl alcohol It is apparent that the aldehyde selectively permeates in comparison with the alcohols and the water. In particular MBAD can be separated effectively from MBA, which besides shows a lower concentration in the permeate than in the retentate ($\alpha_{alcohol, water}$ is less than 1). On the other hand, BAD can be concentrated at much higher values in the permeate ($\alpha_{BAD, water}$>200). The relatively high separation factors of aldehydes with respect to the alcohols show that the membranes are suitable to recover the aldehydes in the permeate and, at the same time, to avoid significant losses of the alcohols. The results obtained for the binary or ternary mixtures considered in these experiments are the basis for the choice of the membrane, but they have been also verified in the real reacting system with complex and varying compositions, since it is known that interactions between the different compounds can modify the permeation properties.

Example 5

Figure 5A:
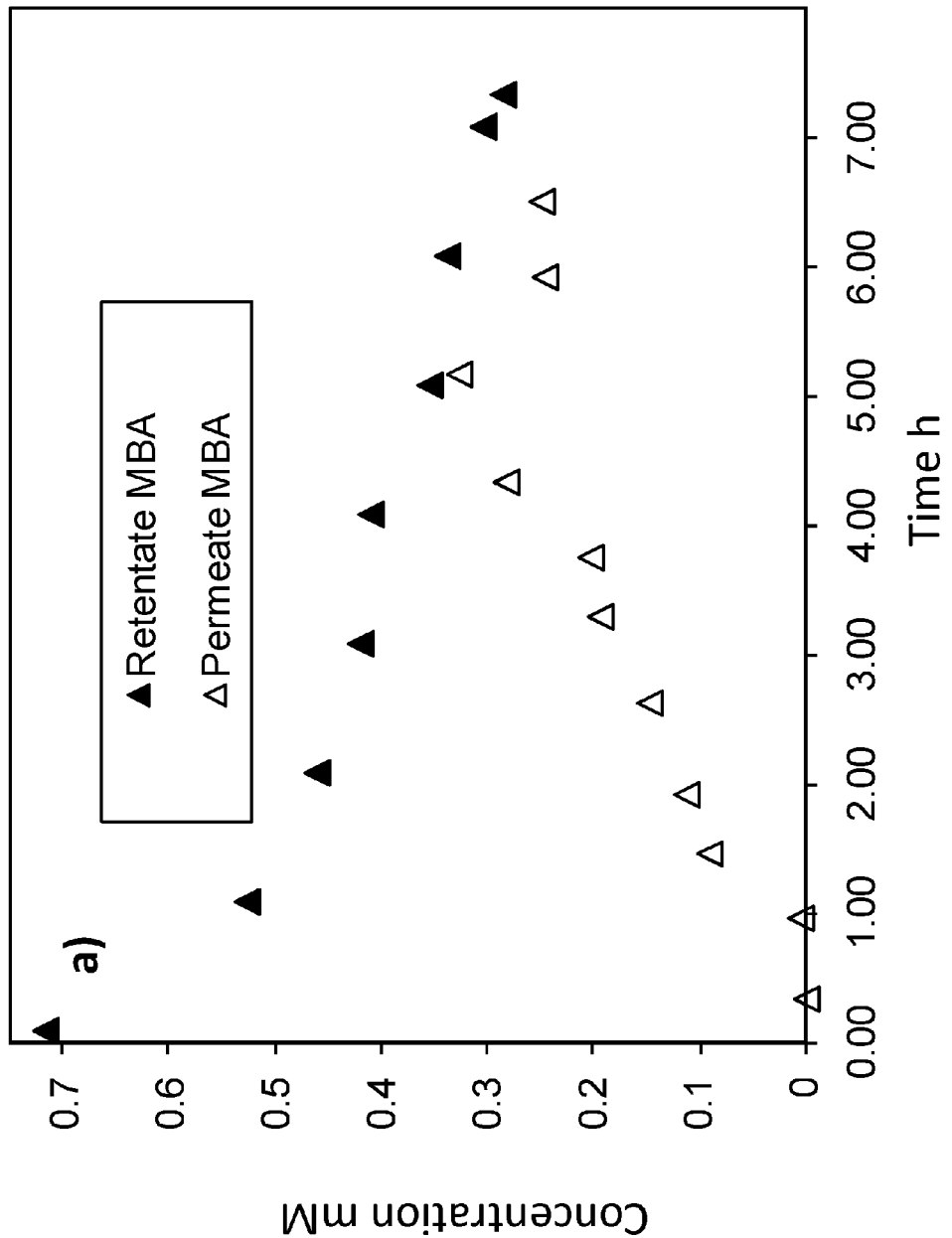
FIG. 5 shows the time profiles in the retentate and in the permeate of the alcohol (a) and of the aldehyde (b) during a representative experiment with the integrated process.
Figure 5B:
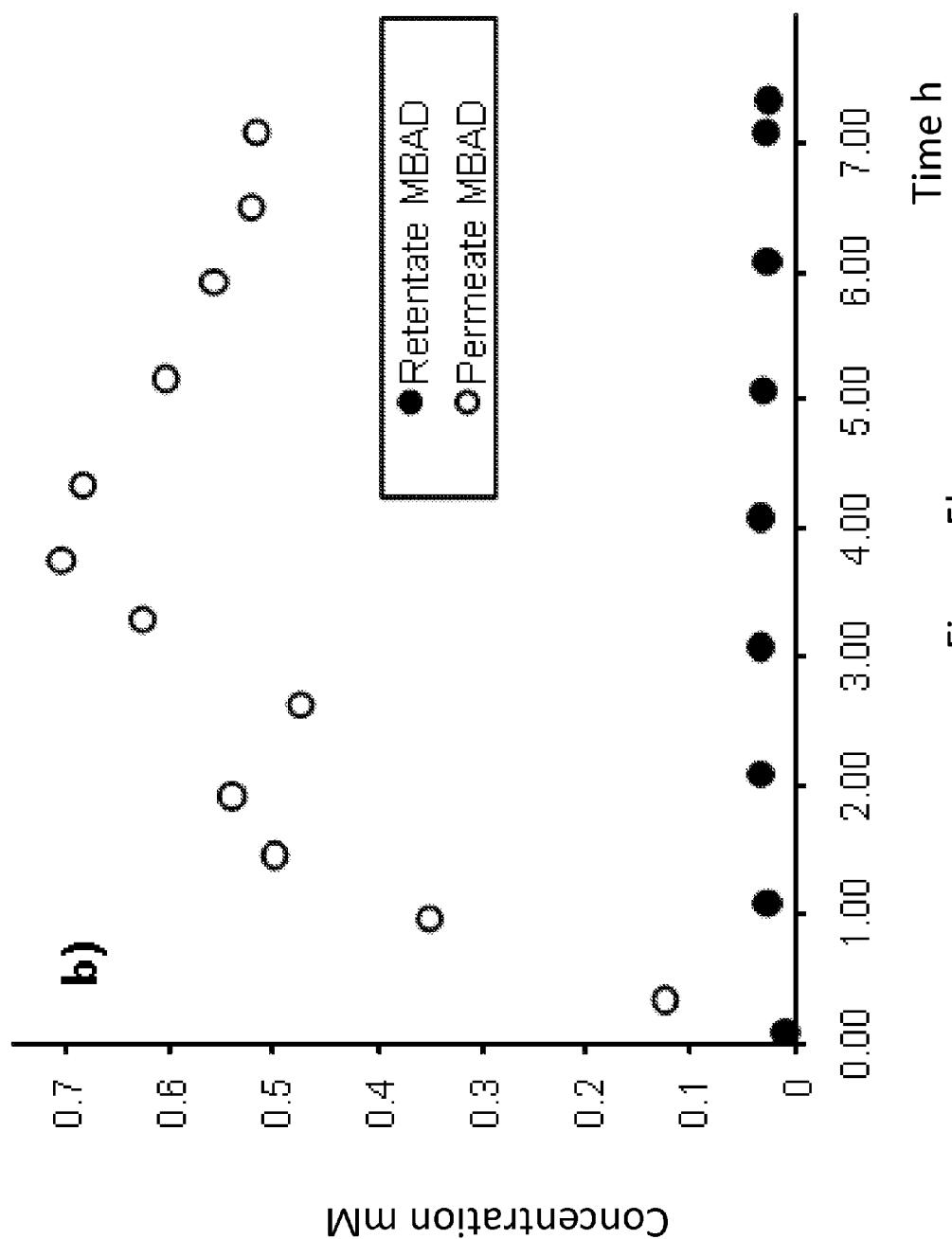

The results which can be obtained in an experiment integrating photocatalysis and pervaporation where MBAD is obtained starting from MBA are illustrated in FIGS. 5a and 5b. The same apparatus previously described and schematically represented in FIG. 1 has been used inserting along the recycle two pervaporation modules for a total membrane area of 320 cm$^2$. Part of the reactor was covered by an aluminum foil to reduce the active volume of the reactor, so that the lighted length was about 8 cm instead of 27.5 cm. The temperature was maintained at 60° C.

In this case, the calculated characteristic time of disappearance of MBA is 3.38 h, the ratio between the residence time in the reactor 2 and the MBA characteristic time of disappearance is about 0.00095 and the ratio between the residence time in the pervaporation unit 3 and the MBA characteristic time of disappearance is about 0.00012.

The concentration of the alcohol in the permeate increases during the experiment, probably as a consequence of the swelling of the polymer induced by the aldehyde, but remains below the value of the concentration in the retentate, confirming that the membrane does not significantly remove the alcohol. On the contrary the selective recovery of the aldehyde in the permeate can be important since at any time its concentration appears to be much higher in the permeate than in the retentate (see FIG. 5b).

Of course the values of the concentration in FIG. 5 depend on the operating conditions and in particular on the parameter, R, the ratio between the rate of the photocatalytic oxidation and the rate of permeation.

In FIG. 6 the quantities of alcohol and aldehyde present in the retentate and cumulatively collected in the permeate are plotted vs. time for the same experiment FIG. 5 refers to.

Figure 6A:
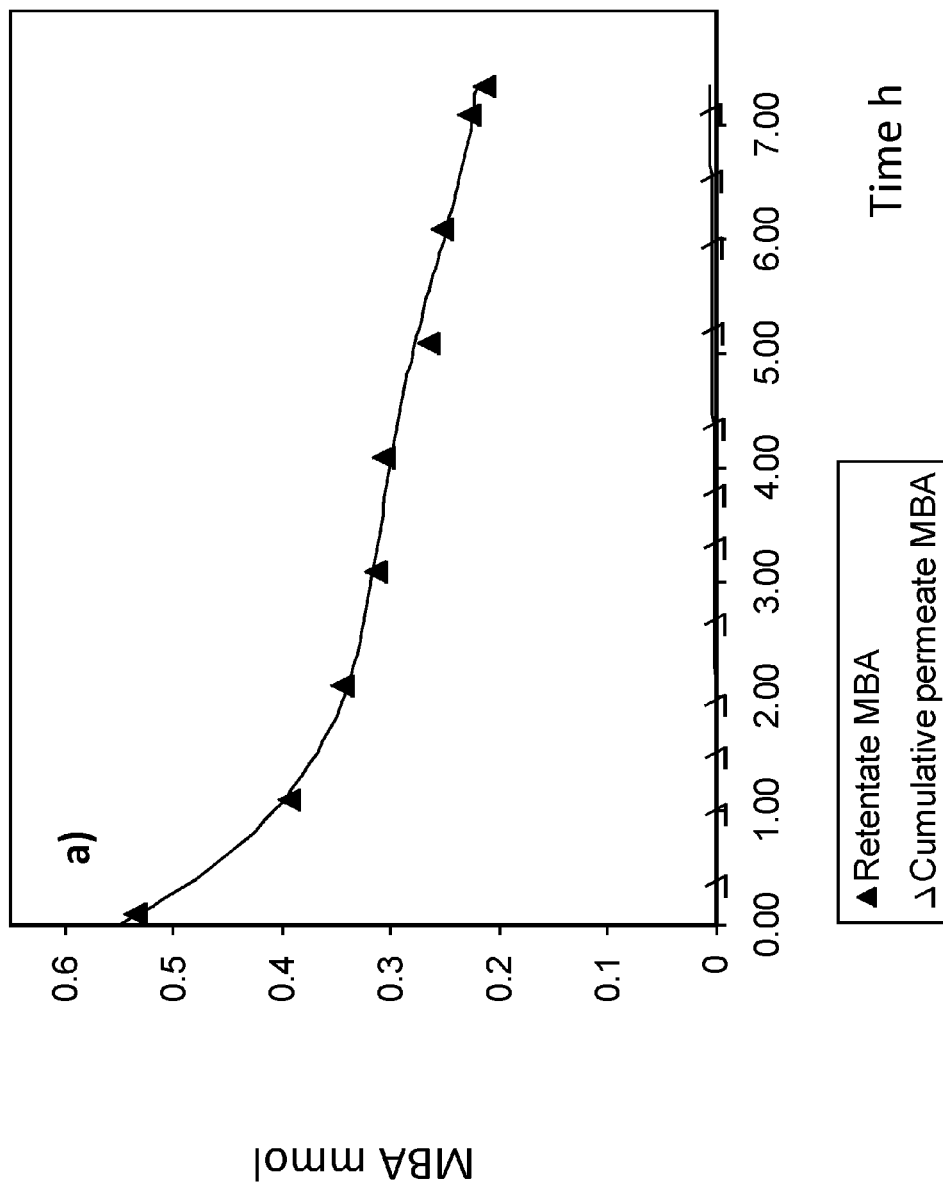
Figure 6B:
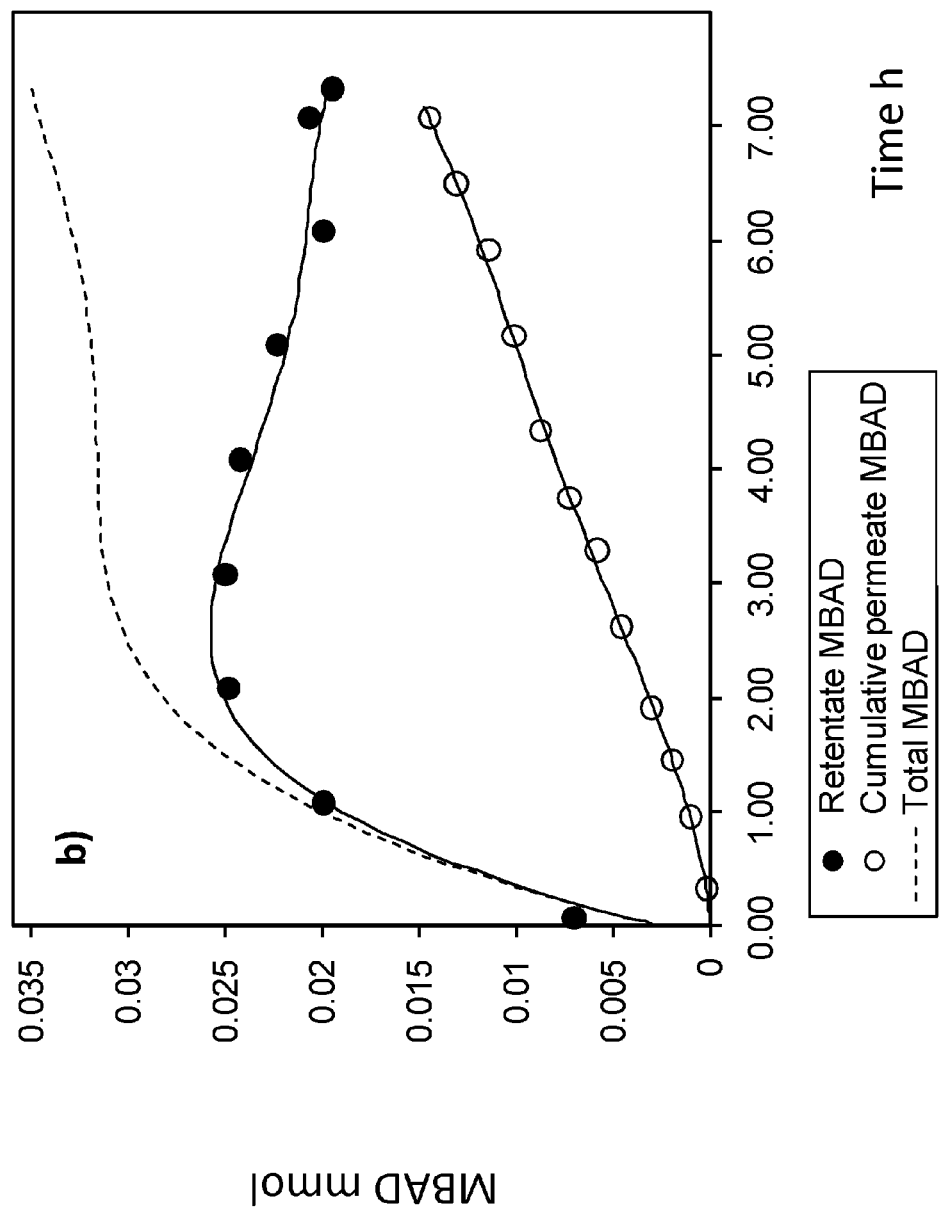

FIG. 6 shows that the membrane removes from the system a negligible amount of the original reagent (see FIG. 6a), whereas a significant amount of aldehyde is cumulatively recovered in the permeate (FIG. 6b). Note also that the curve of the total amount of produced aldehyde is continuously increasing, while, as it was observed previously, without the separation process a maximum is reached at a given time and after then, at longer times, the amount of aldehyde in the system decreases. Operating at lower values of R, which can be obtained by increasing the area of the membrane, the recovery of the aldehyde can be even more effective, particularly at the beginning of the process. For a continuous process lower values of R permit to reach high recovery rate of the aldehyde and to limit the steady state value of the aldehyde in the recycle.

Figure 7:
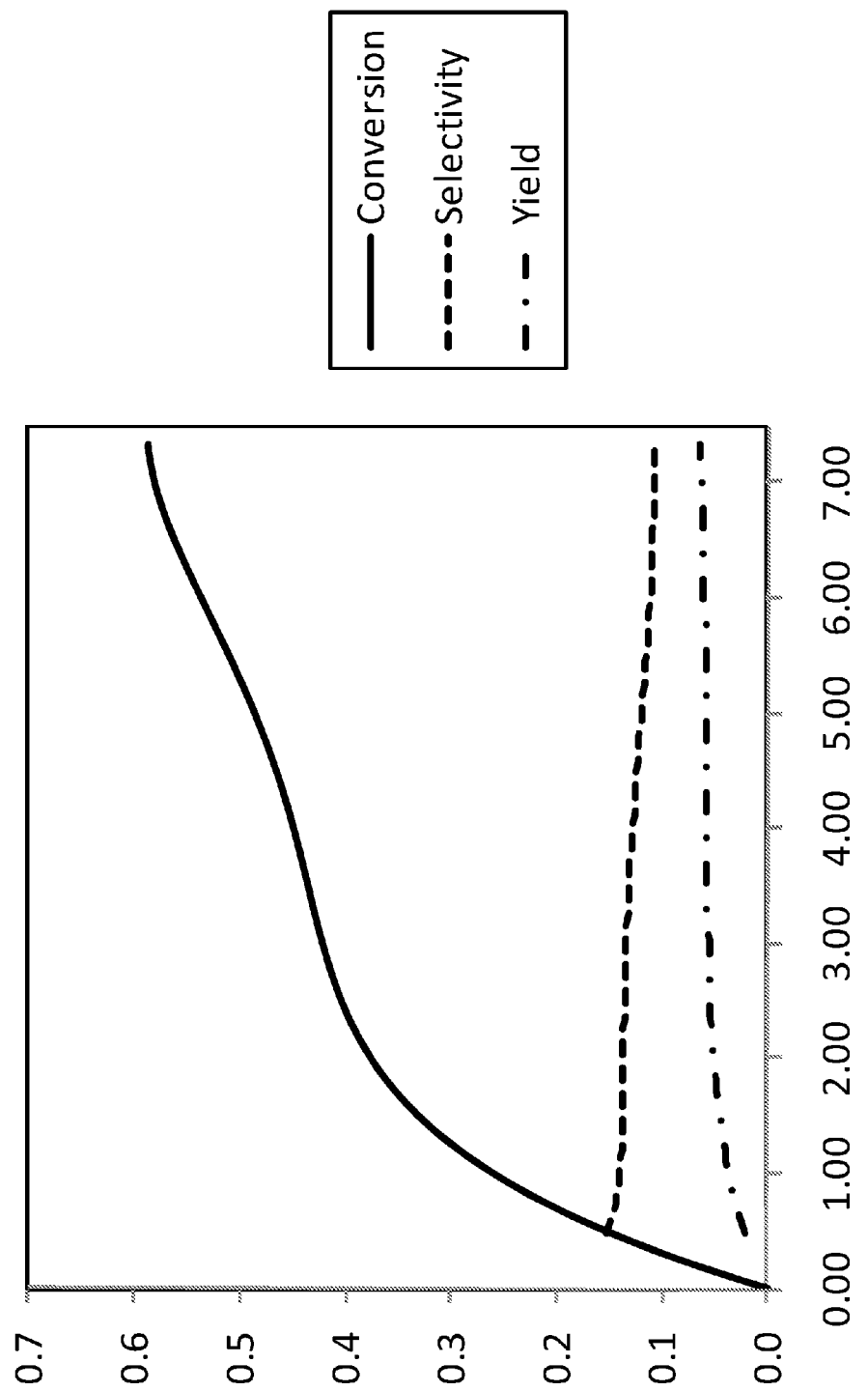

An examination of the values of the conversion, of the selectivity and the yield, reported in FIG. 7, reveals that the yield increases with the time and the selectivity slightly decreases with the time, however selectivity could be maintained almost constant at its initial value (the highest obtainable value) by augmenting the area of the membrane. In the photocatalytic process without pervaporation the selectivity is usually decreasing with time, since the consecutive degradation reaction starts as soon as the aldehyde is produced. The conversion obviously increases with time but with a singular behaviour. In fact in the experiment under investigation the conversion shows an acceleration after approximately 3 hours in association with the decrease of the concentration of the aldehyde (see FIG. 6b). Actually, as mentioned previously, the aldehyde is competitive with the alcohol and its recovery in the permeate is beneficial for the rate of the process. In spite of the possible decrease of the selectivity, the yield, which is the product of the selectivity by the conversion, increases with time. On the contrary, in a photocatalytic process without pervaporation the yield begins to decline at relatively short times when the conversion approaches an asymptotic value and the selectivity decreases due to the consecutive reaction which degrades the aldehyde.

Table II reports the values of the BAD selectivity obtained at similar values of the conversion in two experiments carried on in the same reactor, with the same photocatalyst and at the same operative conditions, the only difference being the presence of pervaporation (integrated process) or its absence (only photocatalysis).

TABLE II

Values of the BAD selectivity obtained at a given value of the conversion with or without pervaporation.

| Photocatalysis | Conversion | Selectivity |
|---|---|---|
| With pervaporation | 0.205 | 0.511 |
| Without pervaporation | 0.211 | 0.325 |

The higher value is obtained in the integrated process thanks to the continuous recovery of the aldehyde.

Example 6

In this example the photocatalytic reaction of ferulic acid, (E)-3-(4-hydroxy-3-methoxy-phenyl)prop-2-enoic acid, has been coupled with the pervaporation to recover vanillin while it is produced.

The scheme of the plant adopted in this experiment is the same in FIG. 1 and disclosed in the present application.

A slurry photocatalytic annular reactor with a volume of about 150 mL has been initially fed with a 4 mM aqueous solution of ferulic acid in water with 0.3 g/L of suspended of Aeroxide Degussa P25 titania powders. A total volume of 600mL of the reactant mixture is continuously recirculated by a peristaltic pump with a flow rate of 4 L/min through the reactor and through a pervaporation module containing a PEBAX (polyether block amide) membrane with an active surface area=$4.4 \times 10^{-3}$ $m^2$. The permeate pressure is maintained at 5 mBar and the temperature at 65° C.

In this case, the calculated characteristic time of disappearance of ferulic acid is 3.96 h, the ratio between the residence time in the reactor 2 and the ferulic acid characteristic time of disappearance is about 0.00016 and the ratio between the residence time in the pervaporation unit 3 and the ferulic acid characteristic time of disappearance is about 0.000019.

The switch on of an 8 W linear blacklight lamp at time t=0.5 h activated the reaction and at the same time the collection of the permeate started.

Figure 12:
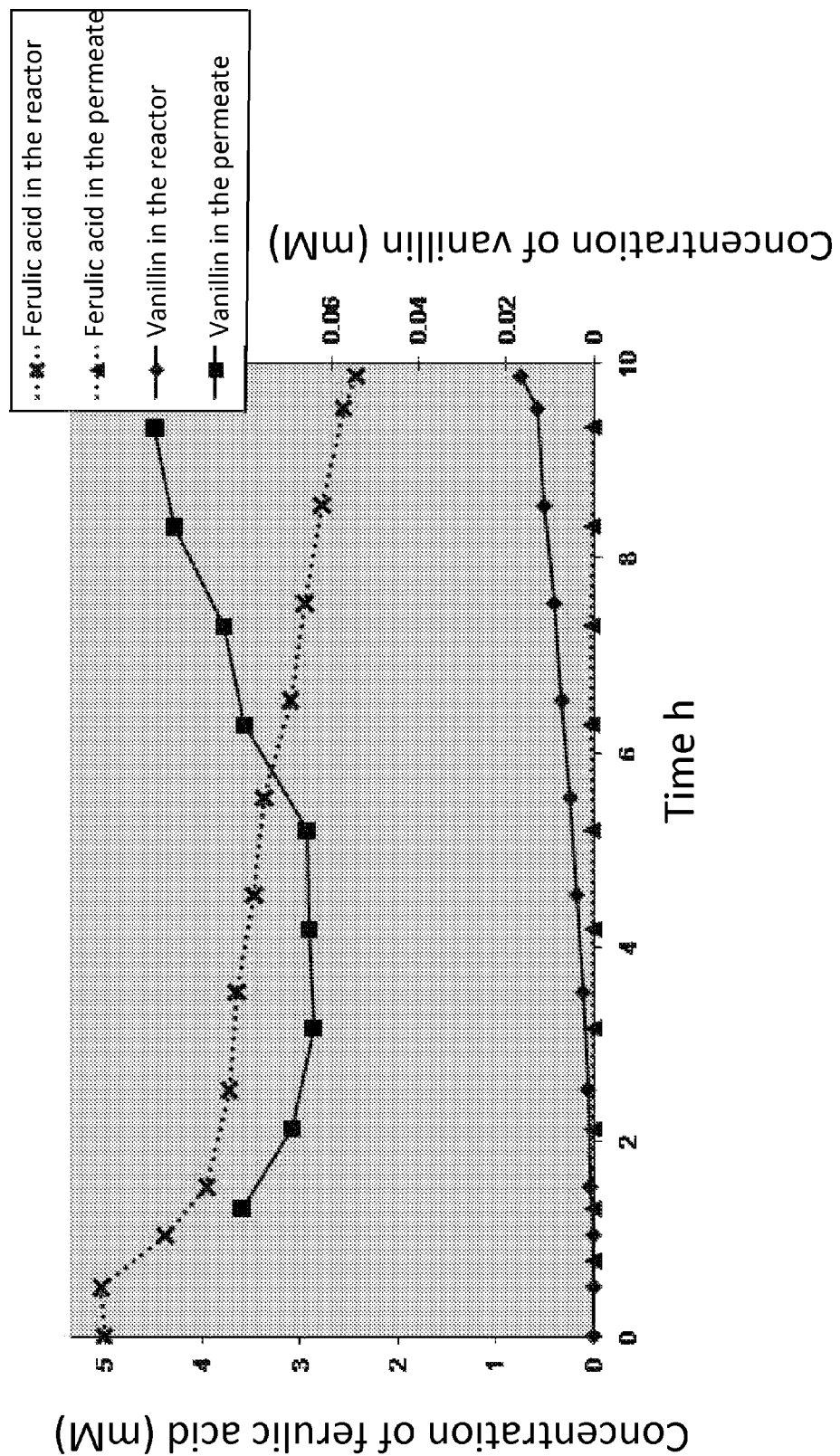
FIG. 12 shows the concentrations of ferulic acid (reagent) and vanillin (product) in the reactor and in the permeate in the process illustrated in Example 6.

The concentrations of ferulic acid and of vanillin are plotted in FIG. 12.

It is observed that the pervaporation membrane allows the recovery of the vanillin, which is much more concentrated in the permeate than in the reactor, so that its photocatalytic oxidation is largely avoided. At the same time ferulic acid is restrained in the reactor since its passage into the permeate is absolutely negligible. Furthermore the photocatalyst powders are absent in the permeate.

The invention claimed is:

1. A process for the preparation of an aromatic aldehyde comprising oxidizing corresponding starting compound in aqueous medium, and separating aldehyde from said medium by simultaneous pervaporation through an organophilic membrane.

2. The process according to claim 1, wherein said process is carried out in semi-continuous or continuous mode.

3. The process according to claim 2, wherein unreacted, corresponding starting compound is recycled.

4. The process according to claim 1, wherein the corresponding starting compound is a primary aryl aliphatic alcohol.

5. The process according to claim 4, wherein said primary alcohol, is selected from the group consisting of benzyl alcohol, 4-methoxybenzyl alcohol, 4-hydroxy-3-methoxybenzyl alcohol, 4-nitrobenzyl alcohol, 4-methylbenzyl alcohol, 4-(trifluoro)methylbenzyl alcohol, 4-tertiarybutylbenzyl alcohol, 4-hydroxylbenzyl alcohol and 2-phenylethanol.

6. The process according to claim 1, wherein the corresponding starting compound is an alkenyl benzene.

7. The process according to claim 6, wherein said alkenyl benzene is selected from the group consisting of 4-allyl-2-methoxy phenol, 2-methoxy-4-(1-propenyl)phenol, hydroxylated alkenyl aromatics, and (E)-3-(4-hydroxy-3-methoxy-phenyl)prop-2-enoic acid.

8. The process according to claim 1, wherein said oxidizing comprises catalytic photo-oxidation.

9. The process according to claim 8, wherein in said catalytic photo-oxidation a catalyst is titanium dioxide.

10. The process according to claim 1, wherein the membrane used in the pervaporation is selected from the group consisting of polyoctylmethyl siloxane (POMS) or polydimethyl siloxane (PDMS), PEBA (polyether block amide) and PTMSP (polytrimethylsilylpropyne).

11. The process according to claim 1, wherein the ratio between residence times of said medium both in a reactor, wherein said oxidation is carried out, as well as in a pervaporation unit, wherein said pervaporation occurs, and the characteristic time of disappearance of said corresponding starting compound is equal to or lower than 0.1.

12. The process according to claim 11, wherein said ratio is equal to or lower than 0.01.

13. The process according to claim 1, wherein said membrane is loaded with fillers.

14. A plant for the production of an aromatic aldehyde comprising:
a. a reactor in which said aromatic aldehyde is obtained from a reaction medium by oxidizing a corresponding starting compound,
b. a pervaporation unit connected downstream of said reactor including an organophilic membrane selectively permeable to said aldehyde in order to separate said aldehyde from the reaction medium as a permeate of the pervaporation unit, and
c. flow moving means so arranged as to move the reaction medium through the reactor and the pervaporation unit with a flow rate such that the residence time of the reaction medium in the reactor and in the pervaporation unit is equal or lower than 1/10 of the characteristic time of disappearance of the corresponding starting compound.

15. The plant according to claim 14, wherein a recycling line connecting said pervaporation unit to said reactor, in order to recycle a retentate of the pervaporation unit to the reactor, is provided.

16. The plant according to claim 15, wherein a feeding tank is provided in said recycling line in order to feed said reactor.

17. The plant according to claim 16, wherein said tank is provided with heating and mixing means.

18. The plant according to claim 14, wherein radiating means are associated with said reactor in order to perform, inside the reactor, a photo-oxidation reaction.

19. The plant according to claim 14, wherein a selectively operating purge line is provided in a line connecting the reactor to the pervaporation unit.

20. The plant according to claim 14, wherein a selectively operating feed line is provided in said recycling line.

* * * * *